(12) United States Patent
Takata et al.

(10) Patent No.: US 10,748,649 B2
(45) Date of Patent: Aug. 18, 2020

(54) SIMILAR CASE RETRIEVAL APPARATUS, SIMILAR CASE RETRIEVAL METHOD, NON-TRANSITORY COMPUTER-READABLE STORAGE MEDIUM, SIMILAR CASE RETRIEVAL SYSTEM, AND CASE DATABASE

(71) Applicant: Panasonic Corporation, Osaka (JP)

(72) Inventors: Kazutoyo Takata, Fukui (JP); Kazuki Kozuka, Fukui (JP); Kenji Kondo, Fukui (JP); Hirohiko Kimura, Fukui (JP); Toyohiko Sakai, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 16/162,569

(22) Filed: Oct. 17, 2018

(65) Prior Publication Data
US 2019/0051401 A1 Feb. 14, 2019

Related U.S. Application Data

(63) Continuation of application No. 15/420,375, filed on Jan. 31, 2017, now Pat. No. 10,133,846, which is a continuation of application No. 14/792,292, filed on Jul. 6, 2015, now Pat. No. 9,594,871, which is a
(Continued)

(30) Foreign Application Priority Data

Aug. 1, 2013 (JP) ................. 2013-160367

(51) Int. Cl.
*G06K 9/00* (2006.01)
*G16H 30/20* (2018.01)
(Continued)

(52) U.S. Cl.
CPC ......... *G16H 30/20* (2018.01); *G06F 16/5838* (2019.01); *G06F 19/00* (2013.01);
(Continued)

(58) Field of Classification Search
CPC ........................... G06T 2207/30096
See application file for complete search history.

(56) References Cited

U.S. PATENT DOCUMENTS 6,282,305 B1  8/2001  Huo et al.
2006/0159321 A1  7/2006  Takeo et al.
(Continued)

FOREIGN PATENT DOCUMENTS

JP  2010-000133  1/2010
JP  2010-227207  10/2010

OTHER PUBLICATIONS

International Search Report of PCT Application No. PCT/JP2014/003237 dated Sep. 9, 2014 with English translation.
(Continued)

*Primary Examiner* — Oneal R Mistry
(74) *Attorney, Agent, or Firm* — Wenderoth, Lind & Ponack, L.L.P.

(57) ABSTRACT

A similar case retrieval apparatus includes: a lesion portion acquirer that acquires partial images including lesion portion images, an image feature extractor that extracts image features of each of the plurality of partial images; a location information acquirer that acquires location information of each of the partial images; a lateral position determiner that determines the right organ or the left organ in which each of the lesion portions exists based on the location information; a unilateral distribution identifier that determines whether or not a distribution of the lesion portions is a unilateral distribution; and a similar case retriever that retrieves case data from a case database including both case data for the unilateral distribution in the right organ and case data for the unilateral distribution in the left organ when the unilateral distribution identifier identifies that the distribution of the lesion portions is the unilateral distribution.

4 Claims, 11 Drawing Sheets

Related U.S. Application Data continuation of application No. PCT/JP2014/003237, filed on Jun. 17, 2014.

(51) Int. Cl.
| | |
|---|---|
| *G16H 50/70* | (2018.01) |
| *G16H 10/60* | (2018.01) |
| *G06F 16/583* | (2019.01) |
| *G06T 7/73* | (2017.01) |
| *G06F 19/00* | (2018.01) |
| *G06K 9/46* | (2006.01) |
| *G06T 7/00* | (2017.01) |
| *A61B 5/08* | (2006.01) |
| *A61B 5/107* | (2006.01) |
| *A61B 6/00* | (2006.01) |

(52) U.S. Cl.
CPC ......... *G06F 19/321* (2013.01); *G06K 9/4604* (2013.01); *G06T 7/0012* (2013.01); *G06T 7/0014* (2013.01); *G06T 7/73* (2017.01); *G16H 10/60* (2018.01); *G16H 50/70* (2018.01); *A61B 5/08* (2013.01); *A61B 5/107* (2013.01); *A61B 6/5217* (2013.01); *A61B 2576/02* (2013.01); *G06T 2207/10081* (2013.01); *G06T 2207/10088* (2013.01); *G06T 2207/10132* (2013.01); *G06T 2207/30061* (2013.01); *G06T 2207/30068* (2013.01); *G06T 2207/30096* (2013.01)

(56) References Cited

U.S. PATENT DOCUMENTS

| | | | | |
|---|---|---|---|---|
| 2007/0237377 | A1* | 10/2007 | Oosawa | G06F 19/321 382/128 |
| 2007/0280525 | A1 | 12/2007 | Basilico et al. | |
| 2008/0107323 | A1* | 5/2008 | Ratner | G06T 7/0012 382/132 |
| 2008/0109323 | A1 | 5/2008 | Leach et al. | |
| 2009/0259139 | A1 | 10/2009 | Stepien et al. | |
| 2010/0080757 | A1* | 4/2010 | Haaga | A61B 5/0263 424/9.3 |
| 2011/0099032 | A1 | 4/2011 | Miyasa et al. | |
| 2011/0122138 | A1* | 5/2011 | Schmidt | G06K 9/6253 345/440 |
| 2011/0123073 | A1 | 5/2011 | Gustafson | |
| 2011/0182489 | A1 | 7/2011 | Chang et al. | |
| 2012/0123239 | A1 | 5/2012 | Han et al. | |
| 2012/0189176 | A1* | 7/2012 | Giger | G06K 9/6253 382/128 |
| 2013/0035957 | A1* | 2/2013 | Gossler | A61B 5/055 705/3 |
| 2015/0379723 | A1* | 12/2015 | Reda | A61B 6/03 382/131 |

OTHER PUBLICATIONS

Mitsutaka Nemoto et al., "Improvement of Tumor Detection Performance in Mammograms by Feature Selection from a Large Number of Features and Proposal of Fast Feature Selection Method", D-II vol. J88-D-II, No. 2, IEICE, 2005, pp. 416-426 with partial English translation.

Ryosuke Urayama et al., "Extraction of lung region from 3D thoracic CT images with diffuse pulmonary diseases by use of graph cut and statistical atlas", IEICE, MI2012-88, 2013, pp. 135-138 with partial English translation.

\* cited by examiner

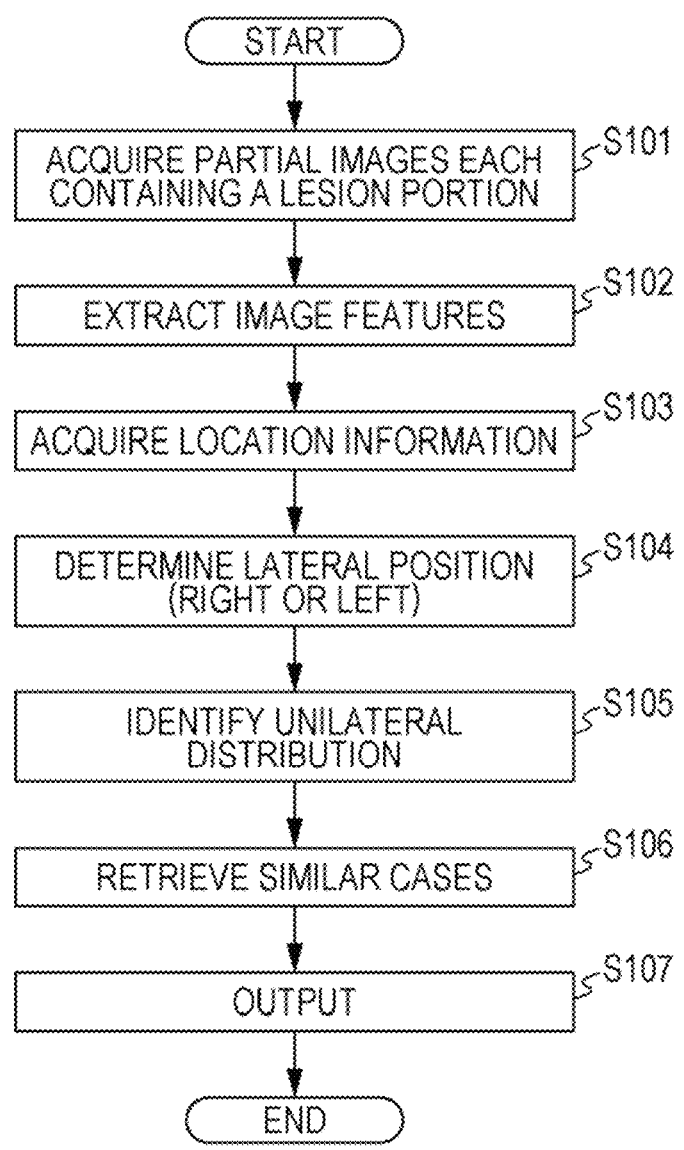

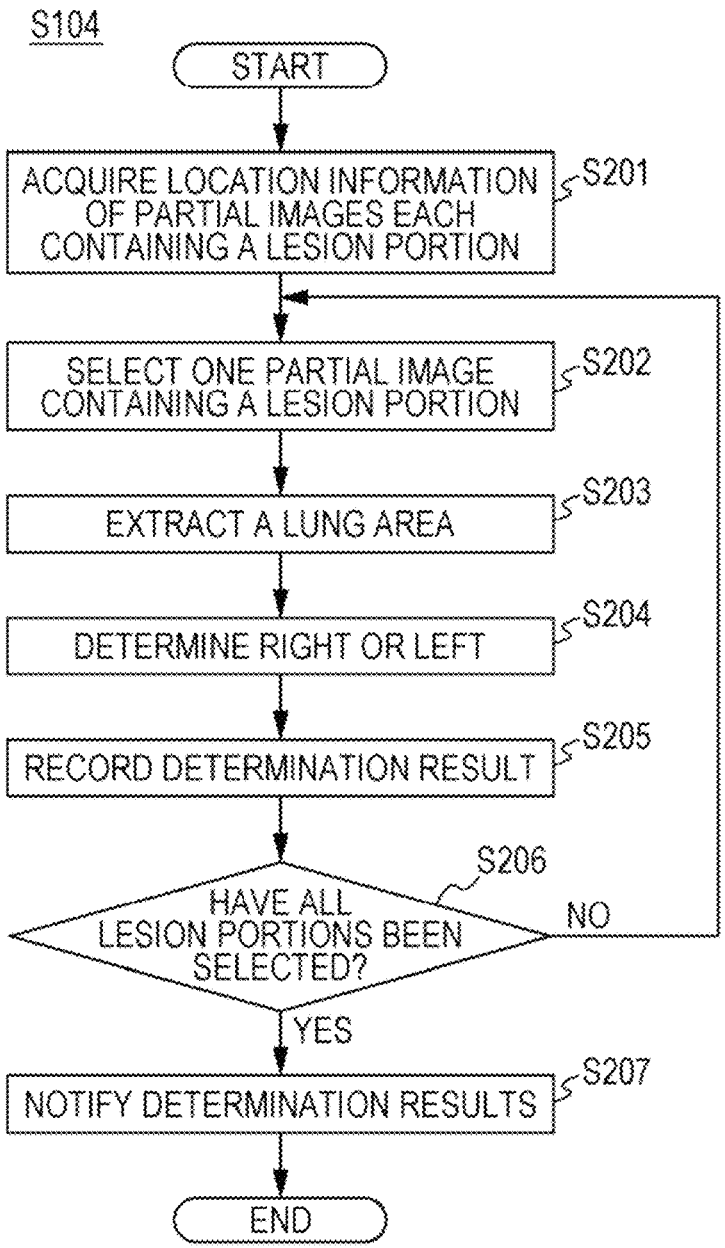

FIG. 9
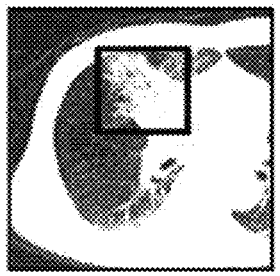
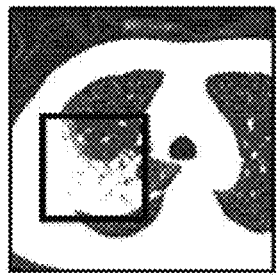
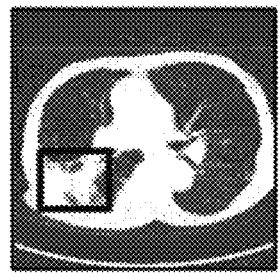
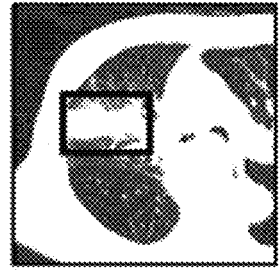
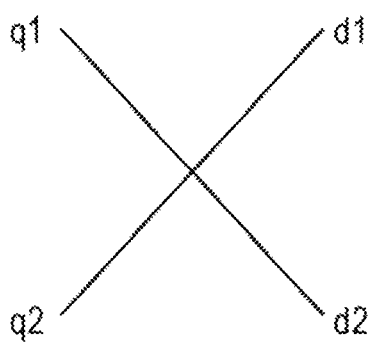

FIG. 10A
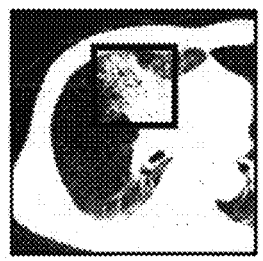
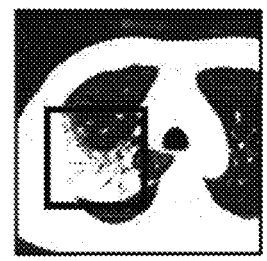
RIGHT LUNG    RIGHT LUNG
UNILATERAL DISTRIBUTION
FIG. 10B
ONE LUNG
(RIGHT LUNG, RIGHT LUNG)
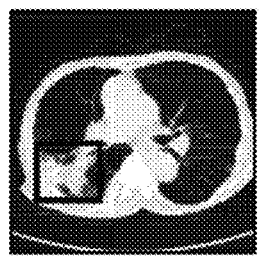
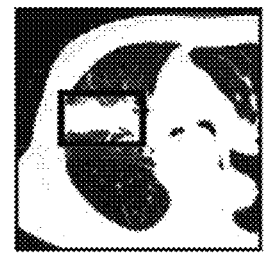
FIG. 10C
ONE LUNG
(LEFT LUNG, LEFT LUNG)
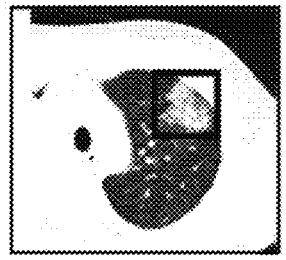
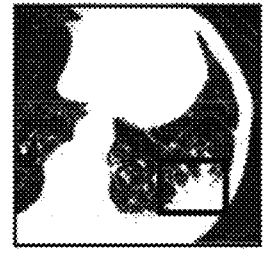

SIMILAR CASE RETRIEVAL APPARATUS, SIMILAR CASE RETRIEVAL METHOD, NON-TRANSITORY COMPUTER-READABLE STORAGE MEDIUM, SIMILAR CASE RETRIEVAL SYSTEM, AND CASE DATABASE

BACKGROUND

1. Technical Field

The present disclosure relates to similar case retrieving techniques.

2. Description of the Related Art

Such a conventional apparatus is known that provides, as a similar case, the same mammographic image every time when the same region of interest is specified, even if the manner of specifying the region of interest varies depending on a doctor, who is a user (see PTL 1 of Patent Literature).

CITATION LIST

Patent Literature

PTL 1: Unexamined Japanese Patent Publication No. 2010-133

Non-Patent Literatures

NPL 1: "Improvement of Tumor Detection Performance in Mammograms by Feature Selection from a Large Number of Features and Proposal of Fast Feature Selection Method" by M. Nemoto, A. Shimizu, Y. Hagihara, H. Kobata, S. Nawano, The IEICE (Institute of Electronics, Information and Communication Engineers of Japan) Transactions (Japanese Edition) D-II, Vol. J88-D-II, No. 2, pp. 416-426, February 2005

NPL 2: "Extraction of lung region from 3D thoracic CT images with diffuse pulmonary diseases by use of graph cut and statistical atlas" by R. Urayama, R. Xu, Y. Hirano, S. Kido, The Technical Report of The Proceeding of The Institute of Electronics, Information and communication Engineers of Japan, Medical Imaging (MI), Vol. 112, No. 411, pp. 135-138, January 2013

However, similar case retrieval cannot appropriately be performed with the configuration disclosed by PTL 1 when plural lesion portions exist in a pair of right and left organs such as a pair of lungs.

SUMMARY

One non-limiting and exemplary embodiment provides a similar case retrieval apparatus that can appropriately perform a similar case retrieval when plural lesion portions exist in a pair of organs.

In one general aspect, the techniques disclosed here feature a similar case retrieval apparatus that includes: a lesion portion acquirer that acquires a plurality of partial images from a plurality of interpretation target images related to a pair of right and left organs, the plurality of partial images including a plurality of lesion portion images of lesion portions, each of the plurality of partial images including a lesion portion image that is one of the plurality of lesion portion images; an image feature extractor that extracts one or more image features of each of the plurality of partial images; a location information acquirer that acquires location information of each of the plurality of partial images; a lateral position determiner that determines the right organ or the left organ in which each of the lesion portions exists based on the location information; a unilateral distribution identifier that determines, based on the determination results by the lateral position determiner, whether or not a distribution of the lesion portions is a unilateral distribution in which the lesion portions are distributed unilaterally in either the right organ or the left organ; and a similar case retriever that retrieves case data from a case database including both case data for the unilateral distribution in the right organ and case data for the unilateral distribution in the left organ, based on the one or more image features extracted by the image feature extractor and image features of images contained in the case database, when the unilateral distribution identifier identifies that the distribution of the lesion portions is the unilateral distribution, an image feature of an image contained in each of the retrieved case data being similar to at least one of the one or more image features extracted by the image feature extractor.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

It should be noted that general or specific embodiments may be implemented as a system, an apparatus, a method, an integrated circuit, a computer program, or a computer-readable storage medium, or may be realized as any combination of a system, an apparatus, a method, an integrated circuit, a computer program and a storage medium. The computer-readable storage medium may include a non-volatile storage medium such as a CD-ROM (Compact Disc-Read Only Memory).

The similar case retrieval apparatus in accordance with the present disclosure can appropriately perform similar case retrieval when plural lesion portions exist in a pair of organs.

BRIEF DESCRIPTION OF THE DRAWINGS

FIG. 5 is a flowchart showing an overall processing flow that is performed by the similar case retrieval apparatus in accordance with the exemplary embodiment;

FIG. 6 is a flowchart showing a detailed processing flow of a lateral position determination;

FIG. 7 is a diagram showing an example of recording a lateral position determination result;

FIG. 9 is a diagram showing an example of combining partial images each containing a lesion portion of an interpretation target image and partial images each containing a lesion portion of case data;

FIG. 10A is a diagram showing an example of query case having a unilateral distribution;

FIG. 10B is a diagram showing an example of retrieved similar case;

FIG. 10C is a diagram showing another example of retrieved similar case;

DETAILED DESCRIPTION

Figure 1:
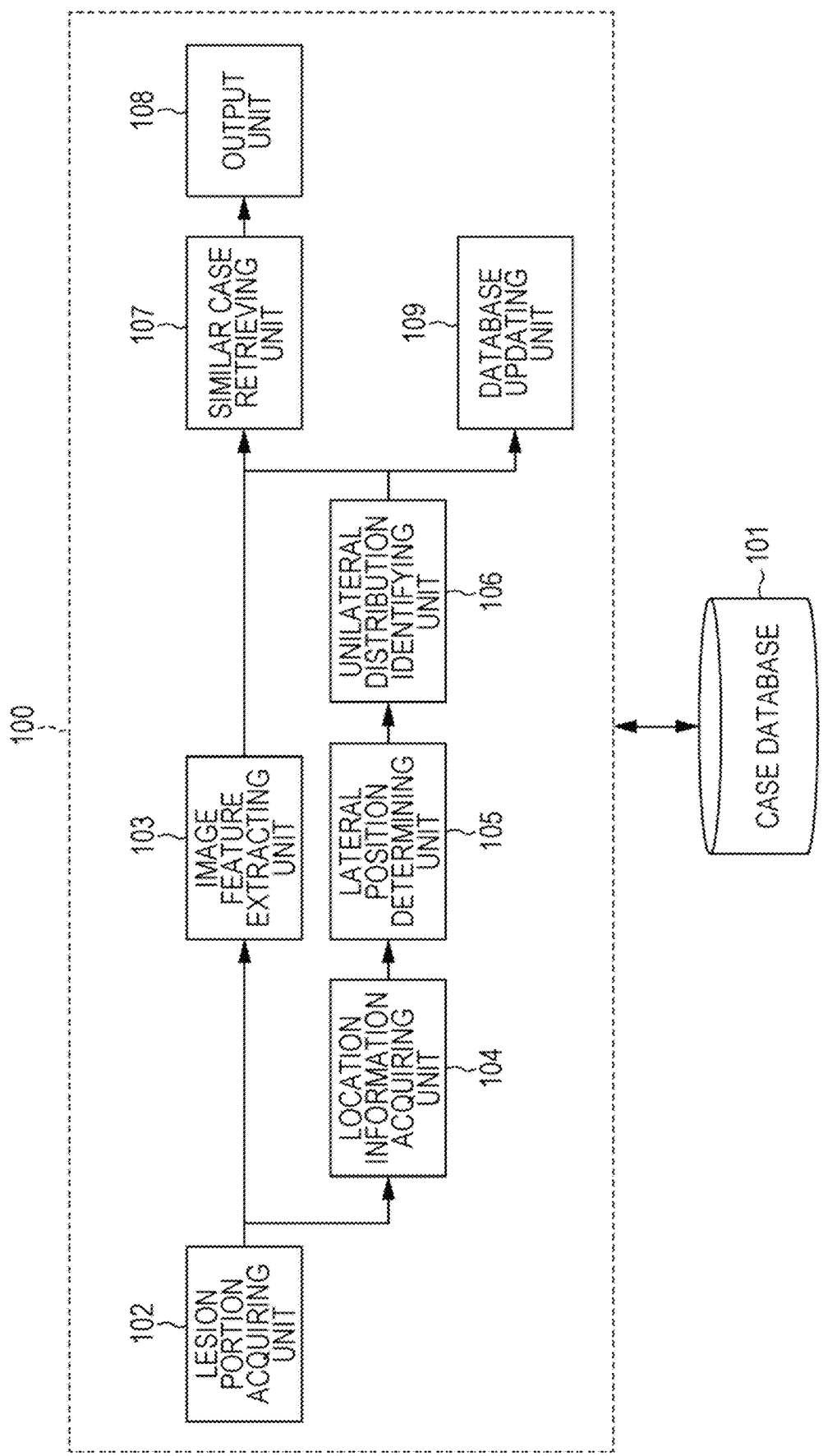
FIG. 1 is a block diagram showing a functional configuration of a similar case retrieval apparatus in accordance with an exemplary embodiment.

Underlying Knowledge Forming Basis of the Present Disclosure

Recently, in the field of diagnostic imaging, digitalization of photographed images and image interpretation reports has been progressed, and it is easy for doctors to share a large amount of data items. As one of secondary uses of these data items, such an effort is expected that supports a decision-making concerning diagnosis by presenting a similar case with respect to an interpreting image, which is an object to be diagnosed, from stored data items.

In retrieving similar cases, it is necessary to retrieve a case that is similar to a lesion in a specified region of interest in the location and distribution of the lesion as well as the morphology of the lesion. Because, diagnosis and treatment policy with respect to lesions may change depending on the locations and/or the distributions of the lesions even if they show the same morphology. As a conventional similar case retrieving technique considering both the lesion morphology and the lesion location, PTL 1 discloses a technique that retrieves similar cases from past cases by using location information and breast density information of a lesion candidate detected from a breast image. According to the method disclosed by PTL 1, it is possible to retrieve cases that are similar in the lesion location as well as the lesion morphology in the region of interest.

In a case of an image diagnosis of a lung field, for example, the distribution of multiple lesions contributing to diagnosis can be broadly categorized into the "unilateral" distribution and the "bilateral" distribution. The unilateral distribution is a state in which plural lesion portions exist in either one of the right lung and the left lung, and the bilateral distribution is a state in which plural lesion portions exist in both of the right lung and the left lung. In other words, when a lesion having a unilateral distribution is input as a search query for similar case retrieval, it is necessary to retrieve cases that are similar in image morphology to the query image from all cases having the unilateral distribution without discriminating the right lung and the left lung.

In the method disclosed by PTL 1, however, cases in the same location are retrieved with a high priority. Accordingly, when a case having a unilateral distribution in one of a pair of lungs is input as a search query, the group of cases each having a unilateral distribution in the other of the pair of lungs (the left lung if the input case is in the right lung) are excluded from the search objects. As a result, even if a similar case having similar image morphology exists in the group of cases each having a unilateral distribution in the other of the pair of lungs, this similar case cannot be retrieved. In other words, the method disclosed by PTL 1 cannot appropriately retrieve similar cases.

This problem is not limited to the cases of lungs, and exists in the cases of the other pairs of organs such as brains, breasts, and kidneys.

Therefore, a first aspect of the present disclosure provides a similar case retrieval apparatus that includes: a lesion portion acquirer that acquires a plurality of partial images from a plurality of interpretation target images related to a pair of right and left organs, the plurality of partial images including a plurality of lesion portion images of lesion portions, each of the plurality of partial images including a lesion portion image that is one of the plurality of lesion portion images; an image feature extractor that extracts one or more image features of each of the plurality of partial images; a location information acquirer that acquires location information of each of the plurality of partial images; a lateral position determiner that determines the right organ or the left organ in which each of the lesion portions exists based on the location information; a unilateral distribution identifier that determines, based on the determination results by the lateral position determiner, whether or not a distribution of the lesion portions is a unilateral distribution in which the lesion portions are distributed unilaterally in either the right organ or the left organ; and a similar case retriever that retrieves case data from a case database including both case data for the unilateral distribution in the right organ and case data for the unilateral distribution in the left organ, based on the one or more image features extracted by the image feature extractor and image features of images contained in the case database, when the unilateral distribution identifier identifies that the distribution of the lesion portions is the unilateral distribution, an image feature of an image contained in each of the retrieved case data being similar to at least one of the one or more image features extracted by the image feature extractor.

This makes it possible to perform a similar case retrieval considering whether or not a distribution of plural lesion portions existing in a pair of organs such as lungs is the unilateral distribution. That is, in a case of the unilateral distribution, a similar case retrieval can be performed so that cases to be retrieved include both of cases which are unilaterally distributed in a right organ and cases which are unilaterally distributed in a left organ. Consequently, it is possible to appropriately perform similar case retrieval.

A second aspect of the present disclosure provides the similar case retrieval apparatus according to the first aspect, wherein the pair of organs are a pair of lungs.

A third aspect of the present disclosure provides the similar case retrieval apparatus according to the first aspect, wherein, when the lesion portion acquirer determines that a first lesion portion contained in an acquired first partial image and a second lesion portion contained in an acquired second partial image are included in a solitary lesion, the lesion portion acquirer does not notify the location information acquirer of location information of the first partial image and location information of the second partial image, and wherein the plurality of partial images includes the acquired first partial image and the acquired second partial image.

This allows only multiple lesions to be the objects that are checked to identify the unilateral distribution. Accordingly, it is possible to prevent reduction of search accuracy.

A fourth aspect of the present disclosure provides the similar case retrieval apparatus according to the third aspect, wherein the lesion portion acquirer determines a lesion as the solitary lesion when a percentage of an area having a normal CT value is equal to or lower than a predetermined threshold value in a tomography image of a tomographic slice plane of one of the pair of organs between a first tomographic slice plane of the organ identified by a tomography image containing the first partial image and a second tomographic slice plane of the of the pair of organs identified by a tomography image containing the second partial image.

A fifth aspect of the present disclosure provides the similar case retrieval apparatus according to the first aspect, further including an output that outputs the case data retrieved by the similar case retriever to an outside.

A sixth aspect of the present disclosure provides the similar case retrieval apparatus according to the first aspect, further including a database updater that registers, in the case database, data including the interpretation target image and information that is the identification result by the unilateral distribution identifier and that indicates whether or not a distribution of a lesion is the unilateral distribution.

This makes it possible to sequentially store the retrieved cases in the database, and thus to automatically increase the number of cases to be searched.

A seventh aspect of the present disclosure provides a similar case retrieval method that includes: acquiring a plurality of partial images from a plurality of interpretation target images related to a pair of right and left organs, the plurality of partial images including a plurality of lesion portion images of lesion portions, each of the plurality of partial images including a lesion portion image that is one of the plurality of lesion portion images; extracting one or more image features of each of the plurality of partial images; acquiring location information of each of the plurality of partial images; determining the right organ or the left organ in which each of the lesion portions exists based on the location information; determining, based on the determination results in the determining the right organ or the left organ, whether or not a distribution of the lesion portions is a unilateral distribution in which the lesion portions are distributed unilaterally in either the right organ or the left organ; and retrieving case data from a case database including both case data for the unilateral distribution in the right organ and case data for the unilateral distribution in the left organ, based on the one or more image features extracted in the extracting one or more image features and image features of images contained in the case database, when the unilateral distribution identifier identifies that the distribution of the lesion portions is the unilateral distribution, an image feature of an image contained in each of the retrieved case data being similar to at least one of the one or more image features extracted in the extracting one or more image features.

A eighth aspect of the present disclosure provides a non-transitory computer-readable storage medium storing a program that causes a computer to execute a similar case retrieval method, the similar case retrieval method that includes: acquiring a plurality of partial images from a plurality of interpretation target images related to a pair of right and left organs, the plurality of partial images including a plurality of lesion portion images of lesion portions, each of the plurality of partial images including a lesion portion image that is one of the plurality of lesion portion images; extracting one or more image features of each of the plurality of partial images; acquiring location information of each of the plurality of partial images; determining the right organ or the left organ in which each of the lesion portions exists based on the location information; determining, based on the determination results in the determining the right organ or the left organ, whether or not a distribution of the lesion portions is a unilateral distribution in which the lesion portions are distributed unilaterally in either the right organ or the left organ; and retrieving case data from a case database including both case data for the unilateral distribution in the right organ and case data for the unilateral distribution in the left organ, based on the one or more image features extracted in the extracting one or more image features and image features of images contained in the case database, when the unilateral distribution identifier identifies that the distribution of the lesion portions is the unilateral distribution, an image feature of an image contained in each of the retrieved case data being similar to at least one of the one or more image features extracted in the extracting one or more image features.

A ninth aspect of the present disclosure provides a similar case retrieval system that includes: a similar case retrieval apparatus; and a case database including a plurality of images, wherein the similar case retrieval apparatus comprises: a lesion portion acquirer that acquires a plurality of partial images from a plurality of interpretation target images related to a pair of right and left organs, the plurality of partial images including a plurality of lesion portion images of lesion portions, each of the plurality of partial images including a lesion portion image that is one of the plurality of lesion portion images; an image feature extractor that extracts one or more image features of each of the plurality of partial images; a location information acquirer that acquires location information of each of the plurality of partial images; a lateral position determiner that determines the right organ or the left organ in which each of the lesion portions exists based on the location information; a unilateral distribution identifier that determines, based on the determination results by the lateral position determiner, whether or not a distribution of the lesion portions is a unilateral distribution in which the lesion portions are distributed unilaterally in either the right organ or the left organ; and a similar case retriever that retrieves case data from the case database including both case data for the unilateral distribution in the right organ and case data for the unilateral distribution in the left organ, based on the one or more image features extracted by the image feature extractor and image features of the plurality of images contained in the case database, when the unilateral distribution identifier identifies that the distribution of the lesion portions is the unilateral distribution, an image feature of an image contained in each of the retrieved case data being similar to at least one of the one or more image features extracted by the image feature extractor.

A tenth aspect of the present disclosure provides a case database that includes a plurality of images, wherein a similar case retrieval apparatus uses the case data base, and wherein the similar case retrieval apparatus comprises: a lesion portion acquirer that acquires a plurality of partial images from a plurality of interpretation target images related to a pair of right and left organs, the plurality of partial images including a plurality of lesion portion images of lesion portions, each of the plurality of partial images including a lesion portion image that is one of the plurality of lesion portion images; an image feature extractor that extracts one or more image features of each of the plurality of partial images; a location information acquirer that acquires location information of each of the plurality of partial images; a lateral position determiner that determines the right organ or the left organ in which each of the lesion portions exists based on the location information; a unilateral distribution identifier that determines, based on the determination results by the lateral position determiner, whether or not a distribution of the lesion portions is a unilateral distribution in which the lesion portions are distributed unilaterally in either the right organ or the left organ; and a similar case retriever that retrieves case data from the case database including both case data for the unilateral distribution in the right organ and case data for the unilateral distribution in the left organ, based on the one or more image features extracted by the image feature extractor and image features of the plurality of images contained in the case database, when the unilateral distribution identifier identifies that the distribution of the lesion portions is the unilateral distribution, an image feature of an image contained in each of the retrieved case data being similar to at least one of the one or more image features extracted by the image feature extractor.

Explanation of Terms

Terms used in the following exemplary embodiment will be explained.

The "image features" include features regarding a shape of an organ or a lesion portion in a medical image, and features regarding brightness distribution in a medical image. For example, NPL 1 of the Non-Patent Literature discloses 490 kinds of features (feature information) as the image features. In the present disclosure also, the image features to be used include several tens to several hundred kinds of image features which are predetermined for each medical image photographing apparatus (modality) used to photograph a medical image and for each target organ.

Further, the medical images in the present disclosure include ultrasound images, CT (Computed Tomography) images or MRI (Magnetic Resonance Imaging) images.

The "unilateral distribution" is a state in which a plurality of lesions exist in either one of a pair of organs, and the "bilateral distribution" is a state in which a plurality of lesions exist in both of a pair of organs. The "multiple lesions" are a plurality of lesions existing at different locations in an organ area, and the "solitary lesion" is a single lesion existing at an arbitrary location in an organ area.

Exemplary Embodiment

Hereinafter, description will be made by taking a pair of lungs as an example of the pair of organs.
Configuration of Apparatus FIG. 1 is a block diagram showing a functional configuration of similar case retrieval apparatus 100 in accordance with an exemplary embodiment.

Similar case retrieval apparatus 100 in FIG. 1 is an apparatus which retrieves a similar case data according to an image interpretation result by an image interpreter from case database 101 in which case data containing medical images have been registered. As shown in FIG. 1, similar case retrieval apparatus 100 includes lesion portion acquiring unit 102, image feature extracting unit 103, location information acquiring unit 104, lateral position determining unit 105, unilateral distribution identifying unit 106, similar case retrieving unit 107, and output unit 108. Database updating unit 109 will be described later. Database updating unit 109 may be omitted.

Hereinafter, details of each component of case database 101 and similar case retrieval apparatus 100 which are illustrated in FIG. 1 will be described in order.

Case database 101 is a storage device including, for example, a hard disk and a memory, and stores therein case data including interpretation image data providing an image interpreter with medical images, and image interpretation information corresponding to the interpretation image data. Here, the interpretation image data are image data used for image diagnosis and stored in an electronic medium. Further, the image interpretation information is information associated with the interpretation image data, and includes documentation data such as patient information and retrieval results.

Figure 2:
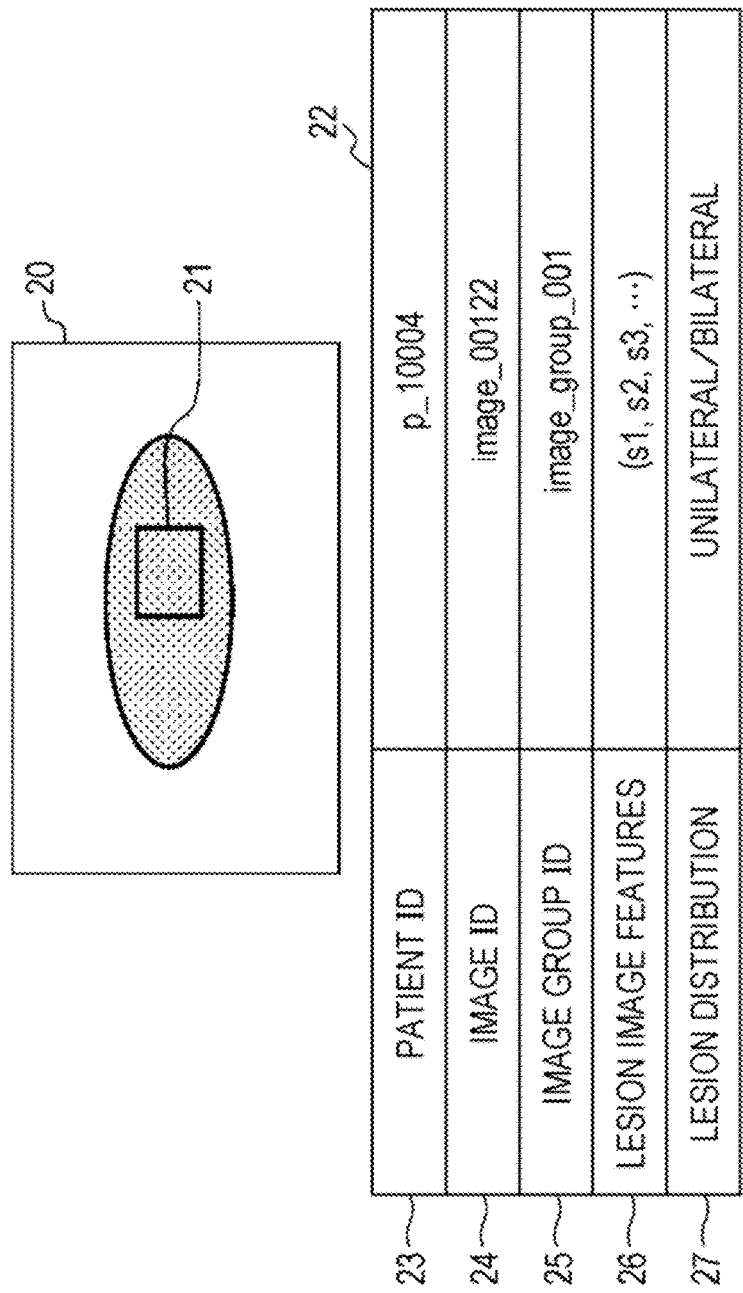
FIG. 2 is a diagram showing an example of case data registered in a case database.

FIG. 2 shows an example of case data registered in case database 101. Lesion region 21 is set in interpretation image data 20 of an organ. Interpretation information 22 includes patient ID 23, image ID 24, image group ID 25 (indicating a group of plural images obtained by one scan in a case of CT images), and additional information including, for example, image features 26 of lesion region 21, and lesion distribution information 27 indicating whether the state of the lesion is the unilateral distribution or the bilateral distribution.

Lesion portion acquiring unit 102 acquires partial images each containing a lesion portion from interpretation target images, or CT images of a lung area here. Each partial image containing a lesion portion is an image of a specific region in an interpretation target image. Lesion portion acquiring unit 102 outputs these acquired partial images each containing a lesion portion to image feature extracting unit 103 and location information acquiring unit 104. Here, a partial image containing a lesion portion may be an entire interpretation target image.

Figure 3:
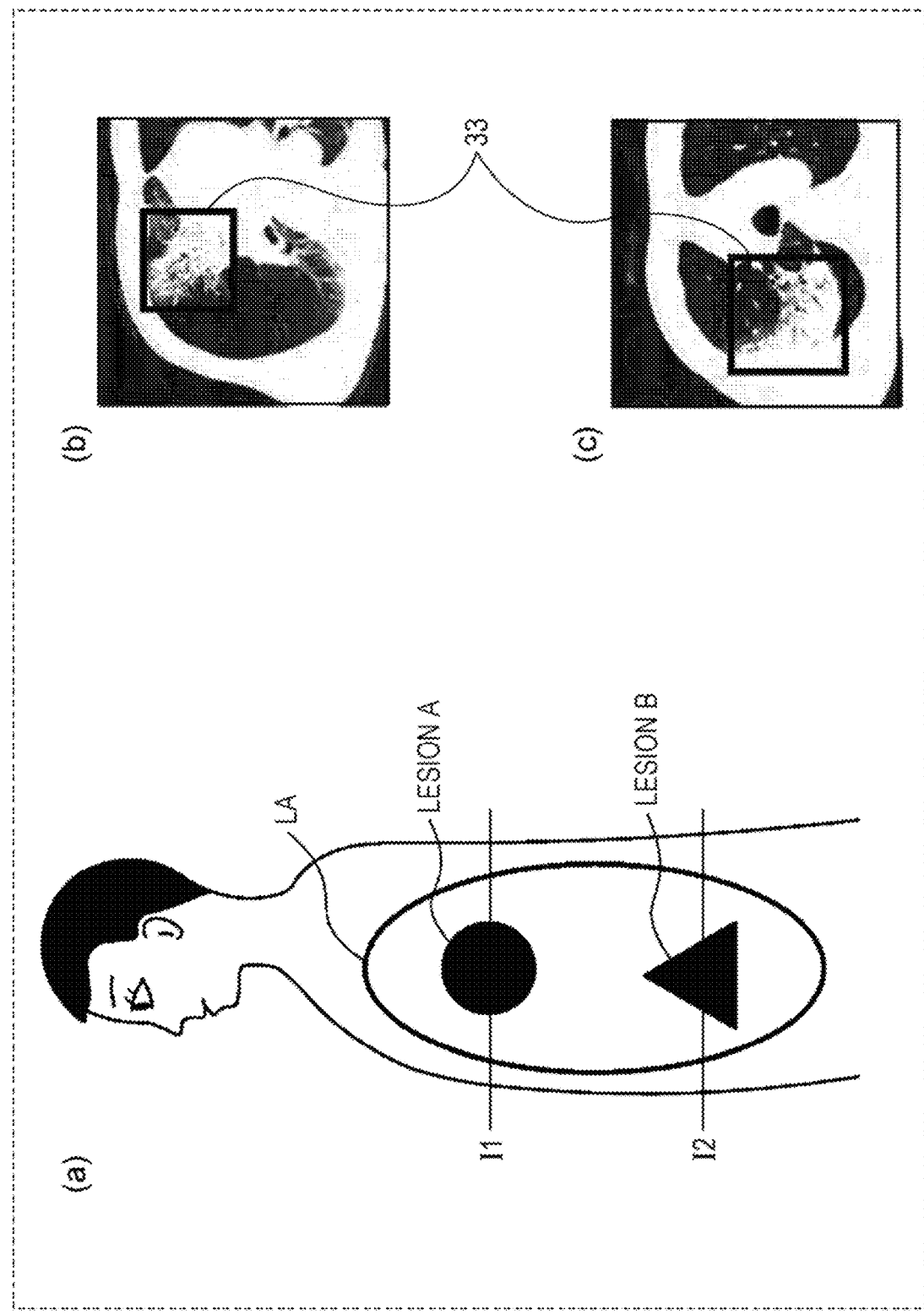
FIG. 3 shows a schematic diagram of lesions in a lung area, a diagram showing an example of tomography image, and a diagram showing another example of tomography image.

An example of acquiring partial images each containing a lesion portion is shown in FIG. 3. When multiple lesions A and B exist in lung area LA as shown in (a) in FIG. 3, tomography images I1 and I2 as respectively shown in (b) and (c) in FIG. 3 are taken in CT image diagnosis. With respect to each of tomography images I1 and I2, a user specifies image region 33 containing a lesion portion. Lesion portion acquiring unit 102 acquires information of image region 33 containing the specified lesion portion, or of a partial image region containing the lesion portion, such as coordinate data of a rectangular frame.

Image feature extracting unit 103 extracts one or more image features from each of the partial images each containing a lesion portion acquired by lesion portion acquiring unit 102, and outputs the extracted image features to similar case retrieving unit 107.

Figure 4:
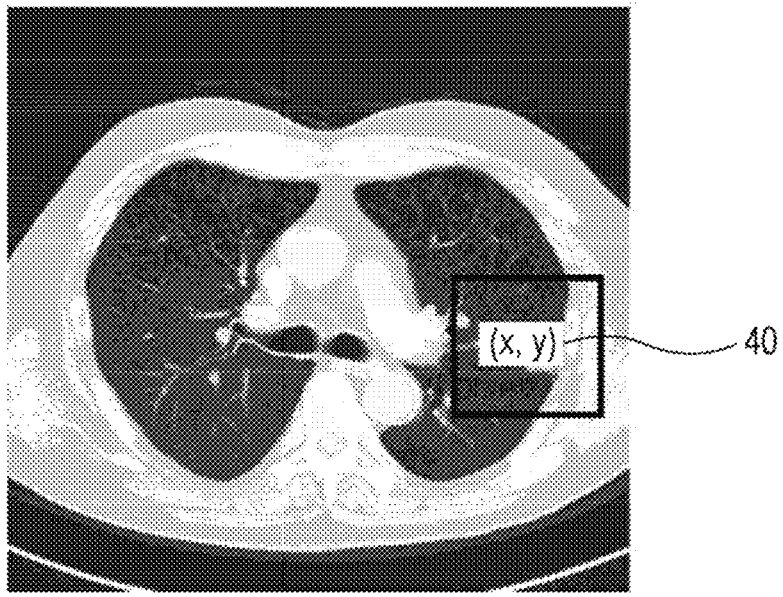
FIG. 4 is a diagram showing an example of acquiring location information of a partial image containing a lesion portion.

Location information acquiring unit 104 acquires location information of the partial images each containing a lesion portion acquired by lesion portion acquiring unit 102, and outputs the acquired location information to lateral position determining unit 105. Specifically, the location information may be the coordinate data of the partial images each containing a lesion portion. For example, as shown in FIG. 4, center coordinates 40 of each partial image containing a lesion portion may be acquired as the location information.

Lateral position determining unit 105 determines in which of the right lung area and the left lung area each of the lesion portions exists based on the location information acquired from location information acquiring unit 104. The determination results are output to unilateral distribution identifying unit 106. Specific determination method will be described later.

Unilateral distribution identifying unit 106 identifies, from the determination results by lateral position determining unit 105, whether the state of the lesions is a unilateral distribution in which the plural lesions exist in only one of the right lung and the left lung. This identification result is output to similar case retrieving unit 107. Specific identification method will be described later.

Similar case retrieving unit 107 retrieves, from case database 101, case data each showing a state similar to that of the interpretation target image, by comparing the image features extracted by image feature extracting unit 103 to image features extracted from medical images contained in case data registered in case database 101. In this retrieval operation, when unilateral distribution identifying unit 106 identifies the state of the lesion contained in the interpretation target image as the unilateral distribution, similar case retrieving unit 107 retrieves, among the case data registered in case database 101, both of case data each showing the unilateral distribution in the right lung and case data each showing the unilateral distribution in the left lung. Specific retrieval method will be described later.

Output unit 108 outputs the case data obtained by similar case retrieving unit 107 to the outside of similar case retrieval apparatus 100, such as an output medium.

Next, an operation of similar case retrieval apparatus 100 configured as above will be described.

Operation

FIG. 5 is a flowchart showing an overall processing flow that is performed by similar case retrieval apparatus 100 shown in FIG. 1.

First, lesion portion acquiring unit 102 acquires a plurality of partial images each containing a lesion portion from a plurality of lung CT images, which are objects to be interpreted, and notifies image feature extracting unit 103 and location information acquiring unit 104 of the acquired partial images each containing a lesion portion (step S101). Here, one CT image contains one partial image containing a lesion portion.

However, one CT image may contain plural partial images each containing a lesion portion.

Image feature extracting unit 103 extracts one or more image features from each of the partial images each containing a lesion portion obtained from lesion portion acquiring unit 102, and notifies similar case retrieving unit 107 of the extracted image features (step S102).

Also, location information acquiring unit 104 acquires location information of the partial images each containing a lesion portion obtained from lesion portion acquiring unit 102, and notifies lateral position determining unit 105 of the acquired location information (step S103).

Next, lateral position determining unit 105 determines in which of the right lung and the left lung each of the plurality of lesions is located based on the location information of the plurality of partial images each containing a lesion portion, the location information obtained from location information acquiring unit 104, and notifies unilateral distribution identifying unit 106 of the determined results (step S104).

FIG. 6 is a flowchart showing a detailed processing flow of step S104, or the lateral position determination processing.

First, lateral position determining unit 105 obtains the location information of the partial images each containing a lesion portion from location information acquiring unit 104. The obtained location information of each partial image containing a lesion portion may, for example, be coordinate data such as center coordinates or center-of-gravity coordinates of the partial image (step S201).

Next, lateral position determining unit 105 selects one partial image containing a lesion portion from the plurality of partial images each containing a lesion portion which have been obtained in step S201 (step S202).

Next, lateral position determining unit 105 extracts a lung area from a tomography image containing the partial image which has been selected in step S202 (step S203). As a method of extracting the lung area, for example, the image processing method as disclosed by NPL 2 of the Non-Patent Literatures may be used to automatically extract the lung area.

Next, with respect to the partial image selected in step S202, lateral position determining unit 105 determines in which of the right side and the left side of the lung area extracted in step S203 the location indicated by the coordinate data of the partial image obtained in step S201 exists (step S204). Specifically, it may be determined, with respect to the partial image selected in step S202, in which side of the extracted lung area the location indicated by the coordinates obtained in step S201 exists.

Next, lateral position determining unit 105 records the determination result obtained in step S204 (step S205). As a recording method, for example, sets of lesion portion ID 70 for identifying each lesion portion and right/left information 71 which is the determination result may be recorded in a list form as shown in FIG. 7.

Next, lateral position determining unit 105 checks whether or not all partial images each containing a lesion portion have been selected. Then, the processing proceeds to step S207 if all partial images have been selected, and returns to step S202 if there remain some partial images each containing a lesion portion which have not yet been selected (step S206).

In step S207, lateral position determining unit 105 notifies unilateral distribution identifying unit 106 of the right/left determination results recorded in step S205.

By performing the processing as shown in FIG. 6, it is possible in step S104 to determine in which of the right lung area and the left lung area each of the plurality of lesion portions exist.

Referring back to FIG. 5, unilateral distribution identifying unit 106 identifies whether the lesion distribution is the unilateral distribution, in which a plurality of lesion portions exist in either one of the right lung and the left lung, from the determination results obtained from lateral position determining unit 105, and notifies similar case retrieving unit 107 of the identified result (step S105). Here, the identification method may, for example, be such that the distribution is identified as the unilateral distribution if all of the right/left determination results obtained from lateral position determining unit 105 are the same. For example, the example shown in FIG. 7 is not the unilateral distribution, because three lesion portions exist in the left lung and one lesion portion exists in the right lung. On the other hand, if all of the lesion portions exist in the left lung, the distribution is identified as the unilateral distribution. However, even in a case where not all lesion portions exist in one of a right organ and a left organ, the distribution may be identified as the unilateral distribution if the lesion portions exist in one of the pair of organs unilaterally to a certain extent.

Next, similar case retrieving unit 107 retrieves case data similar to the state indicated by the interpretation target image from case database 101 by comparing image features extracted from medical images contained in case data registered in case database 101 to image features extracted by image feature extracting unit 103 in step S102. At this time, if the unilateral distribution has been identified by unilateral distribution identifying unit 106 in step S105, case data of the both unilateral distributions, or both the case data of the right lung and the case data of the left lung, are searched (step S106).

Figure 8:
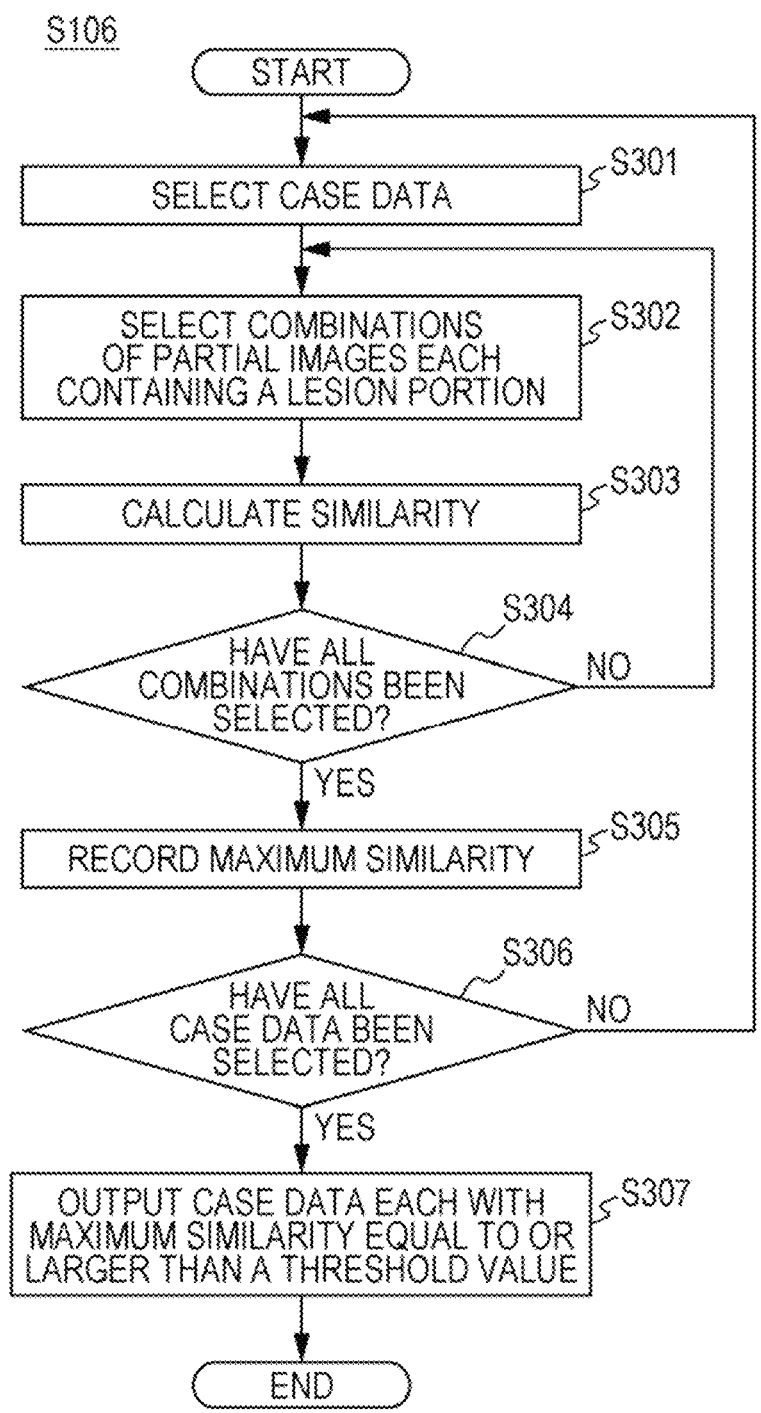
FIG. 8 is a flowchart showing a detailed processing flow of a similar case retrieval.

FIG. 8 is a flowchart showing a detailed processing flow of step S106, or of similar case retrieval processing. Here, it is assumed that the unilateral distribution has been identified in step S105.

First, similar case retrieving unit 107 selects case data each showing the unilateral distribution from case database 101 (step S301). Next, similar case retrieving unit 107 arbitrarily selects combinations of the plurality of partial images each containing a lesion portion obtained in step S101 of FIG. 5 and the plurality of partial images each containing a lesion portion contained in the case data selected in step S301 (step S302).

FIG. 9 shows an example of combination of partial images each containing a lesion portion of an interpretation target image and partial images each containing a lesion portion of case data. In the example shown in FIG. 9, two partial images (q1, q2) each containing a lesion portion is obtained from the interpretation target image in step S101, and two partial images (d1, d2) each containing a lesion portion is obtained from the case data selected in step S301. In this state, there are two possible combinations of the partial images each containing a lesion portion of the interpretation target images and the partial images each containing a lesion portion of the images of the case data, i.e., a combination (q1×d1, q2×d2) and a combination (q1×d2, q2×d1). In step S302, an arbitrary combination (q1×d2, q2×d1 in FIG. 9) is selected from these combinations.

Next, similar case retrieving unit 107 calculates image similarity between the partial images each containing a lesion portion in the combination selected in step S302 (step S303). A specific method of calculating the similarity, for example, may calculate each cosine distance between an image feature vector which is a vector representation of an image feature of a partial image containing a lesion portion of the interpretation target image and an image feature vector of a partial image containing a lesion portion contained in the case data, and calculates a sum of the calculated cosine distances as a similarity. In the example shown in FIG. 9, for example, a sum of a cosine distance between partial image q1 and partial image d2 each containing a lesion portion and a cosine distance between partial image q2 and partial image d1 each containing a lesion portion is calculated as a similarity.

Next, similar case retrieving unit 107 determines whether or not all combinations of the partial images each containing a lesion portion have been selected (step S304). The processing proceeds to step S305 when all combinations have been selected, and returns to step S302 when there remain some combinations which have not yet been selected. Then, in step S305, similar case retrieving unit 107 identifies a maximum similarity from the similarities calculated in step S303, and records the combination of the lesions providing the maximum similarity and the calculated maximum similarity.

Then, similar case retrieving unit 107 determines whether or not all case data recorded in case database 101 and related to the unilateral distribution have been selected (step S306). The processing proceeds to step S307 when all such case data have been selected, and returns to step S301 when there remain some case data which have not yet been selected.

Finally, similar case retrieving unit 107 selects, from the case data recorded in step S305, case data each having a maximum similarity that is equal to or larger than a predetermined threshold value, and outputs the selected case data to output unit 108 (step S307).

By performing the processing as shown in FIG. 8, in step S106, it is possible to retrieve case data each containing an image similar to the interpretation target image from case database 101.

Referring back to FIG. 5, finally, output unit 108 outputs the case data obtained from similar case retrieving unit 107 to an external output medium, for example (step S107).

Here, advantageous effects of discriminating the unilateral distribution in the case of performing the similar case retrieval of multiple lesions will be described. As described above, in the image diagnosis with respect to multiple lesions of a pair of organs such as a pair of lungs, the diagnosis result often varies depending on whether the lesion distribution is the unilateral distribution or the bilateral distribution. Accordingly, with respect to a lesion in a state of the unilateral distribution, it is preferable to retrieve similar cases from past cases each being in a state of the unilateral distribution.

FIG. 10A, FIG. 10B, and FIG. 10C show an example of similar cases retrieved with respect to a query case having the unilateral distribution. With respect to a query case shown in FIG. 10A, similar cases shown in FIG. 10B and FIG. 10C are retrieved. In the convention techniques, such lesion is retrieved that is similar to a lesion to be diagnosed in the lesion distribution location as well as the image morphology of the lesion. Accordingly, with respect to the query case of the right lung shown in FIG. 10A, similar cases in which lesions are distributed in the right lung (the case shown in FIG. 10B) may be preferentially retrieved. On the other hand, the case in which lesions are distributed in the left lung (the case shown in FIG. 10C) may be less possible to be presented to the user, although it is an important reference case having the unilateral distribution, because it may be determined as low in the similarity and thus lowered in the retrieval priority, for the reason that the lesion distribution location is the left, or different from the right.

On the other hand, according to the present exemplary embodiment, similar case retrieval in a case of the unilateral distribution is performed without discriminating the unilateral distribution in the right lung and the unilateral distribution in the left lung. Consequently, with respect to the query case shown in FIG. 10A, cases that are similar in image morphology will preferentially be retrieved, including the cases in which the lesions are distributed in the left lung as shown in FIG. 10C as well as the cases in which the lesions are distributed in the right lung as shown in FIG. 10B. Accordingly, it is possible to retrieve optimum similar cases from all cases that are effective to diagnosis.

According to the present exemplary embodiment, as described above, similar case retrieval apparatus 100 identifies whether or not a plurality of partial images each containing a lesion portion existing in lungs show a state of the unilateral distribution, and, in a case where the unilateral distribution is identified, searches case data each showing the unilateral distribution from both of the case data of the right lung and the case data of the left lung as objects for similar case retrieval. This makes it possible to retrieve appropriate similar cases.

Incidentally, even when a plurality of partial images each containing a lesion portion are acquired by lesion portion acquiring unit 102, these partial images each containing a lesion portion is not always show multiple lesions.

Figure 11C:
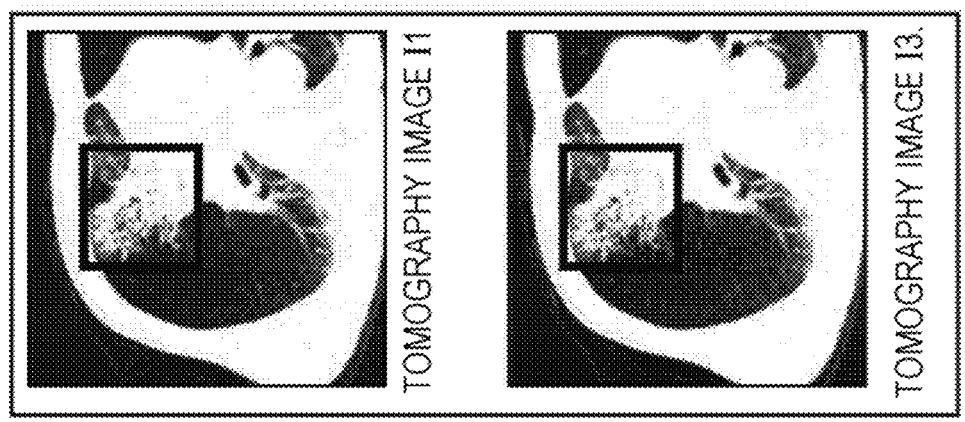
FIG. 11C is a diagram showing an example of tomography images of a solitary lesion.
Figure 11B:
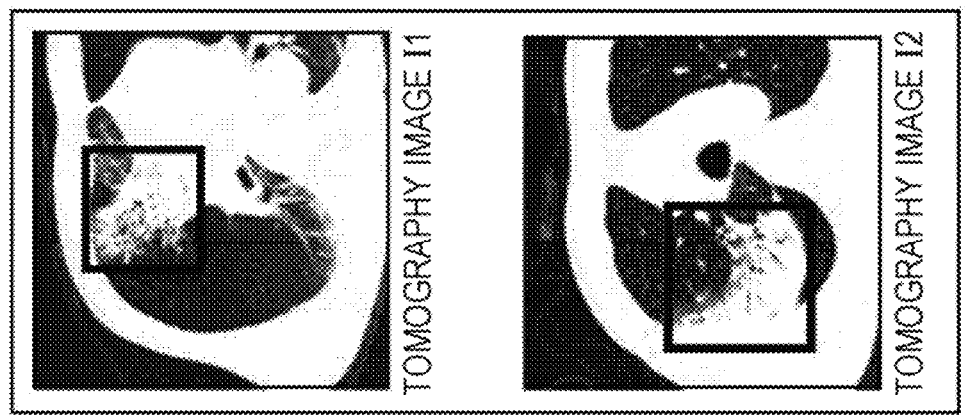
FIG. 11B is a diagram showing an example of tomography images of multiple lesions.
Figure 11A:
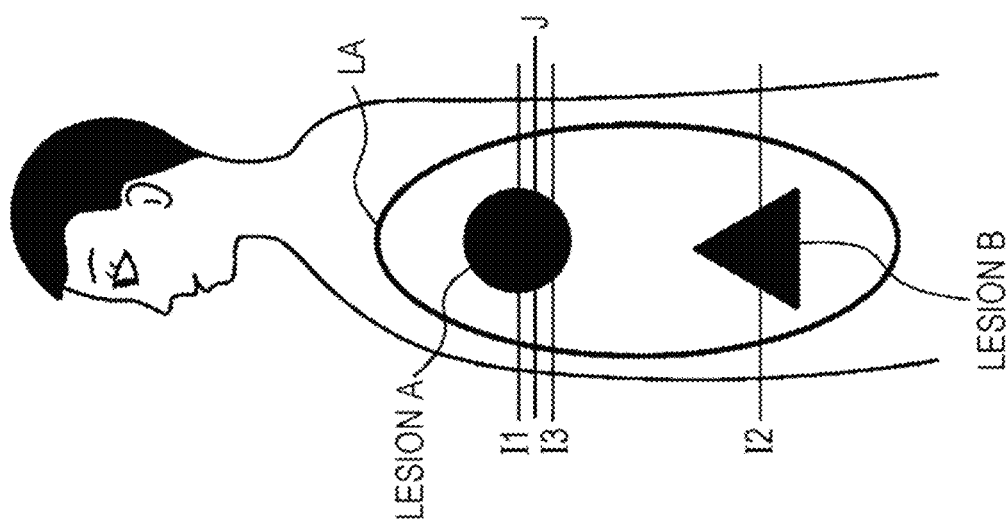
FIG. 11A is a schematic diagram showing lesions in a lung area.

FIG. 11A, FIG. 11B, and FIG. 11C show an example of determining a plurality of lesion portions. When two lesions A and B exist in lung area LA as shown in FIG. 11A, partial images respectively containing the two lesion portions are acquired from tomography images I1 and I2 with respect to two lesions A and B as shown in FIG. 11B. The acquired plural partial images each containing a lesion portion show multiple lesions. However, in a case where only lesion A exists, for example, such a case may possibly occur that two partial images each containing the lesion portion are acquired from tomography images I1 and I3 as shown in FIG. 11C. In this case, a plurality of partial images each containing a lesion portion are acquired, although the existing lesion is a solitary lesion. The solitary lesion and the multiple lesions are findings that show different distributions from each other. Therefore, if these are retrieved as included in the same distribution, a case that is not intended by the user may be retrieved.

Therefore, when lesion portion acquiring unit 102 determines that acquired plural partial images each containing a lesion portion indicate a solitary lesion, lesion portion acquiring unit 102 excludes this solitary lesion from the objects to be checked for identification of the unilateral distribution. That is, lesion portion acquiring unit 102 does not send the information of the solitary lesion to location information acquiring unit 104. Accordingly, only multiple lesions can be the objects to be checked for the unilateral distribution identification, so that it is possible to prevent reduction of retrieval accuracy.

As a method of determining the solitary lesion, it may be determined that a lesion is a solitary lesion if the percentage of an area showing a normal value in an area between plural lesion portions is equal to or lower than a predetermined threshold value. For example, in a case of CT images, it may be determined that a lesion is a solitary lesion if the percentage of an area showing a CT value within a normal range in an image region (e.g., tomography image J shown in FIG. 11A) between plural tomography images each containing a lesion portion (e.g., tomography image I1 and tomography image I3 shown in FIG. 11A) is equal to or lower than a predetermined threshold value. Here, the CT value is a numerical expression of x-ray absorption in human body, and is expressed by a relative value to the value 0 of water (unit: HU).

Also, similar case retrieval apparatus 100 in accordance with the present exemplary embodiment may further includes database updating unit 109 that registers in case database 101 the data containing the interpretation target image and the identification result by unilateral distribution identifying unit 106 when partial images each containing a lesion portion are acquired by lesion portion acquiring unit 102. This makes it possible to sequentially store the retrieved case data in case database 101, so that the number of cases to be retrieved can be automatically increased.

Also, in the present exemplary embodiment, description has been made by taking a pair of lungs as an example of a pair of right and left organs. However, the present disclosure is not limited to this example, and is applicable to other pair of right and left organs such as brains, breasts, and kidneys.

Figure 12:
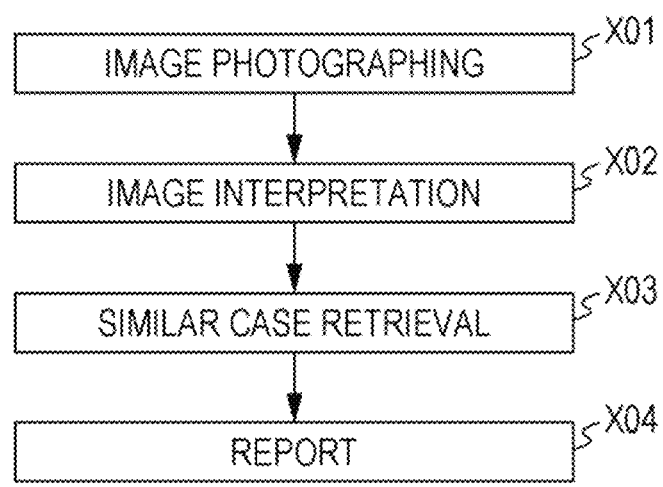
FIG. 12 is a flowchart for showing a position of the similar case retrieval.

Here, supplemental explanation about the similar case retrieval will be made. FIG. 12 is a flowchart for showing a position of the similar case retrieval in accordance with the present disclosure. As shown in FIG. 12, images such as CT images of a patient are photographed first (X01), and then an image interpreter interprets an image case from the photographed images (X02). Then, the image interpreter retrieves similar cases with respect to the interpreted case as necessary (X03), and writes a report by reference to the retrieved similar cases (X04). Here, the similar case retrieval in accordance with the present disclosure corresponds to step X03. That is, the similar case retrieval related to the present disclosure does not fall under the so-called medical activity, that is, a process of surgical, curative or diagnostic treatment of human beings, but is equivalent to a kind of information retrieval technique. Accordingly, the contents of the present disclosure fall under the industrially applicable inventions.

The similar case retrieval apparatus in accordance with the present disclosure have been described in the above based on the exemplary embodiments. However, the present disclosure should not be limited to the exemplary embodiments. For example, various modifications which any person skilled in the art may think of and apply to the present exemplary embodiments, and other embodiments which may be made by combining components of different exemplary embodiments should be included within a scope of the present disclosure without departing from the spirit of the present disclosure.

The above-described similar case retrieval apparatus may specifically be implemented as a computer system including, for example, a microprocessor, a read-only memory (ROM), a random access memory (RAM), a hard disk drive, a display unit, a keyboard, and a mouse. A computer program is stored in the RAM or the hard disk drive. The microprocessor operating according to the computer program allows the similar case retrieval apparatus to achieve their functions. Here, the computer program is configured by combining a plurality of instruction codes indicating instructions for allowing the computer to achieve predetermined functions.

Further, a part or all of the components configuring the above-described similar case retrieval apparatus may be implemented as a large scale integrated circuit known as a system LSI (Large Scale Integration). The system LSI is an ultra multi-function LSI produced by integrating a plurality of construction parts on a single chip, and specifically a computer system configured to include components such as a microprocessor, a ROM, and a RAM. A computer program is stored in the RAM. The microprocessor operating according to the computer program allows the system LSI to achieve its functions.

Furthermore, a part or all of the above-described similar case retrieval apparatus may be implemented as an IC card or monolithic module, which can be detachably attached to the similar case retrieval apparatus. The IC card or the module is a computer system including, for example, a microprocessor, a ROM, and a RAM. The IC card or the module may include the ultra multi-function LSI. The microprocessor operating according to a computer program allows the IC card or the module to achieve its functions. The IC card or the module may also be implemented to be tamper resistant.

Further, the present disclosure may be regarded as the methods described above. Furthermore, the present disclosure may be regarded as a computer program for causing a computer to execute the methods, or as a digital signal including the computer program.

Further, the present disclosure may be regarded as a form in which the computer program or digital signal is recorded in a non-transitory, computer-readable storage medium such as a flexible disk, a hard disk, a CD-ROM, an MO, a DVD, a DVD-ROM, a DVD-RAM, a BD (Blu-ray Disc (registered trademark)), and other semiconductor memories. Furthermore, the present disclosure may be regarded as the digital signal recorded in the non-transitory storage medium.

Further, the present disclosure may be regarded as a form in which the computer program or digital signal is transmitted through an electrical communications line, a wireless or wired communications line, a network represented by the internet, data broadcasting, or the like.

Further, the present disclosure may be regarded as a computer system including a microprocessor and a memory such that the memory stores the computer program and the microprocessor operates according to the computer program.

Further, the present disclosure may be implemented in another independent computer system by transferring the program or digital signal recorded in the non-transitory recording medium or by transferring the program or digital signal through the network or the like.

The present disclosure is applicable to a similar case retrieval apparatus and the like for outputting a similar case with respect to a result of a diagnosis made by an image interpreter.

What is claimed is:

1. A method comprising:
    receiving a first image showing lesion portions distributed unilaterally in a right organ; and
    outputting a second image without reflecting the first image around a vertical axis, the second image being selected from case data including a set of third images, and each of the third images showing lesion portions distributed unilaterally in a left organ,
    wherein the case data does not include one or more fourth images showing lesion portions distributed unilaterally in one or more right organs,
    a first partial image is included in the first image and a second partial image is included in the second image, the first partial image and the second partial image having a predetermined similarity, and
    the first partial image is directly compared with the second partial image without the first partial image and the second partial image being reflected around the vertical axis.

2. The method according to claim 1, wherein
    the predetermined similarity of first partial image and the second partial image is based on a cosine distance between an image feature vector for the first partial image and an image feature vector for the second partial image, and calculating a sum of calculated cosine distances as the predetermined similarity.

3. An apparatus comprising:
    a receiver that receives a first image showing lesion portions distributed unilaterally in a right organ; and
    an output device that outputs a second image without reflecting the first image around a vertical axis, the second image being selected from case data including a set of third and each of the third images showing lesion portions distributed unilaterally in a left organ,
    wherein the case data does not include one or more fourth images showing lesion portions distributed unilaterally in one or more right organs,
    a first partial image is included in the first image and a second partial image is included in the second image, the first partial image and the second partial image having a predetermined similarity, and
    the first partial image is directly compared with the second partial image without the first partial image and the second partial image being reflected around the vertical axis.

4. The apparatus according to claim 3, wherein the predetermined similarity of first partial image and the second partial image is based on a cosine distance between an image feature vector for the first partial image and an image feature vector for the second partial image, and calculating a sum of calculated cosine distances as the predetermined similarity.

* * * * *